(12) United States Patent
Azar

(10) Patent No.: US 7,270,677 B2
(45) Date of Patent: Sep. 18, 2007

(54) POLARIZATION-SENSITIVE VISION PROSTHESIS

(75) Inventor: Dimitri T. Azar, Brookline, MA (US)

(73) Assignee: Massachusetts Eye & Ear Infirmary, Boston, MA (US)

( * ) Notice: Subject to any disclaimer, the term of this patent is extended or adjusted under 35 U.S.C. 154(b) by 0 days.

(21) Appl. No.: 11/421,911

(22) Filed: Jun. 2, 2006

(65) Prior Publication Data

US 2006/0206204 A1    Sep. 14, 2006

Related U.S. Application Data

(62) Division of application No. 10/971,434, filed on Oct. 22, 2004, now Pat. No. 7,141,065.

(51) Int. Cl.
*A61F 2/14* (2006.01)
(52) U.S. Cl. ...................... 623/4.1; 623/6.22
(58) Field of Classification Search ............. 623/4.1, 623/5.11, 5.16, 6.11, 6.17, 6.22, 6.24, 6.27, 623/6.32–6.37, 6.62
See application file for complete search history.

(56) References Cited

U.S. PATENT DOCUMENTS

| | | | |
|---|---|---|---|
| 5,044,743 A | 9/1991 | Ting | ........................... 351/163 |
| 5,408,281 A | 4/1995 | Zhang | |
| 5,653,751 A | 8/1997 | Samiy et al. | |
| 5,800,530 A * | 9/1998 | Rizzo, III | .................. 623/6.22 |
| 5,800,533 A | 9/1998 | Eggleston et al. | |
| 6,413,641 B1 | 7/2002 | Yamasaki et al. | |
| 6,638,304 B2 | 10/2003 | Azar | |
| 6,669,727 B1 | 12/2003 | Young | |
| 6,966,648 B2 | 11/2005 | Miller et al. | |
| 2005/0036109 A1 * | 2/2005 | Blum et al. | .................. 351/168 |

* cited by examiner

*Primary Examiner*—William H. Matthews
(74) *Attorney, Agent, or Firm*—Fish & Richardson P.C.

(57) ABSTRACT

A vision prosthesis includes a first detector disposed to detect a polarization state of light reflected from a retina, and a controller in communication with the first detector. The controller is configured to receive, from the detector, a measurement signal indicative of the polarization state. In response thereto, the controller generates a control signal for causing a change to an optical property of an optical system in optical communication with the retina.

13 Claims, 5 Drawing Sheets

POLARIZATION-SENSITIVE VISION PROSTHESIS

RELATED APPLICATIONS

This application is a divisional of U.S. patent application Ser. No. 10/971,434, filed on Oct. 22, 2004 now U.S. Pat. No. 7,141,065, the entire contents of which are hereby incorporated by reference.

FIELD OF INVENTION

This invention relates to a vision prosthesis, and in particular, to dynamic control of optical characteristics of a vision prosthesis.

BACKGROUND

In the course of daily life, one typically regards objects located at different distances from the eye. To selectively focus on such objects, the focal length of the eye's lens must change. In a healthy eye, this is achieved through the contraction of a ciliary muscle that is mechanically coupled to the lens. To the extent that the ciliary muscle contracts, it deforms the lens. This deformation changes the focal length of the lens. By selectively deforming the lens in this manner, it becomes possible to focus on objects that are at different distances from the eye. This process of selectively focusing on objects at different distances is referred to as "accommodation".

As a person ages, the lens loses plasticity. As a result, it becomes increasingly difficult to deform the lens sufficiently to focus on objects at different distances. To compensate for this loss of function, it is necessary to provide different optical corrections for focusing on objects at different distances.

One approach to applying different optical corrections is to carry different pairs of glasses and to swap glasses as the need arises. For example, one might carry reading glasses for reading and a separate pair of distance glasses for driving. This is inconvenient both because of the need to carry more than one pair of glasses and because of the need to swap glasses frequently.

Bifocal lenses assist accommodation by integrating two different optical corrections onto the same lens. The lower part of the lens is ground to provide a correction suitable for reading or other close-up work while the remainder of the lens is ground to provide a correction for distance vision. To regard an object, a wearer of a bifocal lens need only maneuver the head so that rays extending between the object-of-regard and the pupil pass through that portion of the bifocal lens having an optical correction appropriate for the range to that object.

The concept of a bifocal lens, in which different optical corrections are integrated into the same lens, has been generalized to include trifocal lenses, in which three different optical corrections are integrated into the same lens, and continuous gradient lenses in which a continuum of optical corrections are integrated into the same lens. However, just as in the case of bifocal lenses, optical correction for different ranges of distance using these multifocal lenses relies extensively on relative motion between the pupil and the lens.

Once a lens is implanted in the eye, the lens and the pupil move together as a unit. Thus, no matter how the patient's head is tilted, rays extending between the object-of-regard and the pupil cannot be made to pass through a selected portion of the implanted lens. As a result, multifocal lenses are generally unsuitable for intraocular implantation because once the lens is implanted into the eye, there can be no longer be relative motion between the lens and the pupil.

A lens suitable for intraocular implantation is therefore generally restricted to being a single focus lens. Such a lens can provide optical correction for only a single range of distances. A patient who has had such a lens implanted into the eye must therefore continue to wear glasses to provide optical corrections for those distances that are not accommodated by the intraocular lens.

SUMMARY

A vision prosthesis according to the invention includes an auto-focus mechanism that relies on the difference between the birefringent properties of the fovea, and the birefringent properties of portions of the retina surrounding the fovea, referred to herein as the "circumfovea." By illuminating the retina with polarized light, and measuring the polarization state of light reflected from the retina, it is possible to estimate how much of the reflected light was reflected by the fovea and how much was reflected by the circumfovea. On the basis of this estimate, a controller causes a change in an optical property of an optical system. This, in turn cause a desired change in the estimate.

In one aspect, the vision prosthesis includes a first detector disposed to detect a polarization state of light reflected from a retina; and a controller in communication with the first detector. The controller is configured to receive, from the detector, a measurement signal indicative of the polarization state, In response, the controller generates a control signal for causing a change to an optical property of an optical system in optical communication with the retina.

Some embodiments also include a first polarizer in optical communication with the retina. The first polarizer blocks passage of light having a first polarization state. The first polarizer can include, for example, a first polarizing region of a lens in the optical element.

Embodiments that include a first polarizer optionally include a second detector disposed to detect light passing through the first polarizer. The second detector is configured to provide, to the controller, a signal representative of light passing through the first polarizer.

Embodiments that include a first polarizer can also include a second polarizer in optical communication with the retina. The second polarizer blocks passage of light having a second polarization state orthogonal to the first polarization state.

In some embodiments, the first detector in configured to be implanted in a cornea.

Other embodiments of the vision prosthesis also include those in which the optical system includes an intra-ocular lens, a contact lens, an eyeglass lens, or a natural lens of the eye.

The controller can be configured to generate a control signal at least in part on the basis of a comparison between polarized light reflect from a foveal region of the retina and polarized light reflected from elsewhere on the retina. However, the controller can also be one that is configured to generate a control signal on the basis of a comparison between the polarization state as detected by the first detector and a polarization state associated with light reflected from a fovea of the retina. Or, the controller can be one that is configured to generate a control signal to cause a change to a focal length of the optical system.

In another aspect, the invention includes a vision prosthesis having a controller configured to cause an optical property of an optical element to change in response to a signal indicative of a polarization state of light reflected from a retina.

Another aspect of the invention includes a method for controlling a vision prosthesis by detecting a polarization state of light reflected from a retina and receiving a measurement signal indicative of the polarization state. In response to the signal, a control signal causes a change to an optical property of an optical system in optical communication with the retina.

In some practices, generating a control signal includes comparing polarized light reflected from a foveal region of the retina and polarized light reflected from elsewhere on the retina. The control signal is generated at least in part on the basis of the comparison.

In other practices, generating a control signal includes generating a control signal at least in part on the basis of a polarization state associated with light reflected from a fovea of the retina.

The method can also include causing a change to a focal length of the optical system in response to the control signal.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following detailed description, and from the claims.

DETAILED DESCRIPTION

Figure 1:
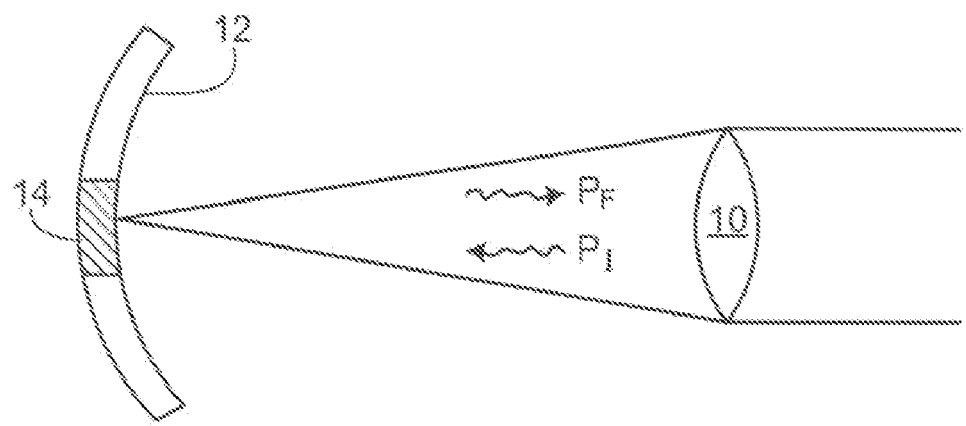
FIG. 1 shows a lens focusing light on the fovea.

FIG. 1 shows polarized light entering a lens 10 and being focused onto a retina 12, and in particular, onto the fovea 14 of the retina. The polarized light is characterized by an incident polarization state $P_I$. In the process of being reflected by the fovea 14, the incident light has its polarization state changed. The foveally-reflected light thus has a reflected polarization state, $P_F$, that differs from the incident polarization state, $P_I$. The extent of this difference corresponds to the birefringent properties of the fovea 14.

Figure 2:
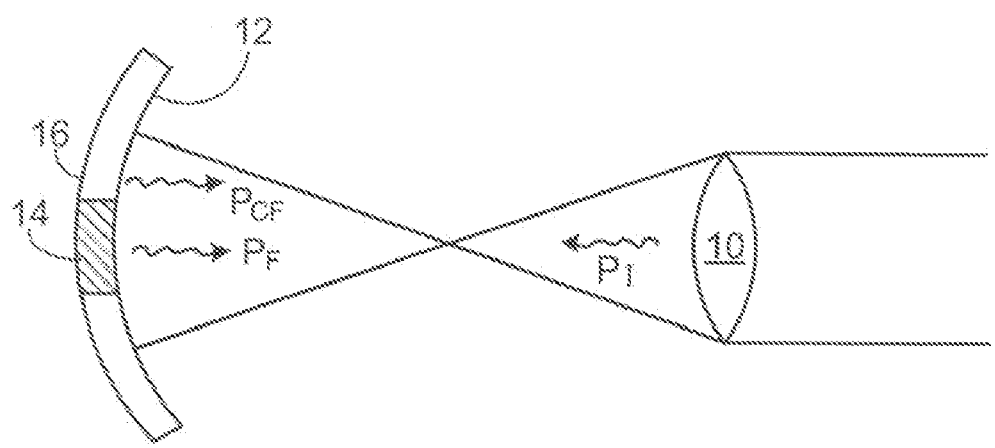
FIG. 2 shows a lens focusing light anterior to the fovea.

FIG. 2 shows polarized light entering a lens 10 that fails to focus onto the fovea 14. In this particular example, the lens 10 brings light to a focus anterior to the retina 12. However, the same principle is at work when the lens 10 brings light to a focus posterior to the retina 12. In both cases, polarized light illuminates both the fovea 14 and the circumfovea 16. The reflected light is therefore a combination of foveally-reflected light, which is characterized by a first polarization state $P_F$, and circumfoveally-reflected light, which is characterized by a second polarization state $P_{CF}$. As a result, the reflected light acquires a net polarization state that depends in part on the relative contributions of the foveal reflection and the circumfoveal reflection.

The difference between the polarization state of the reflected light in FIG. 1 and the polarization state of reflected light in FIG. 2 provides a way to determine whether the lens 10 is correctly focusing light on the fovea 14. When the lens 10 is in focus, the reflection is dominated by foveally-reflected light. Thus, to the extent light reflected from the retina 12 has a polarization state consistent with foveally reflected light, the lens 10 is in focus.

Figure 3:
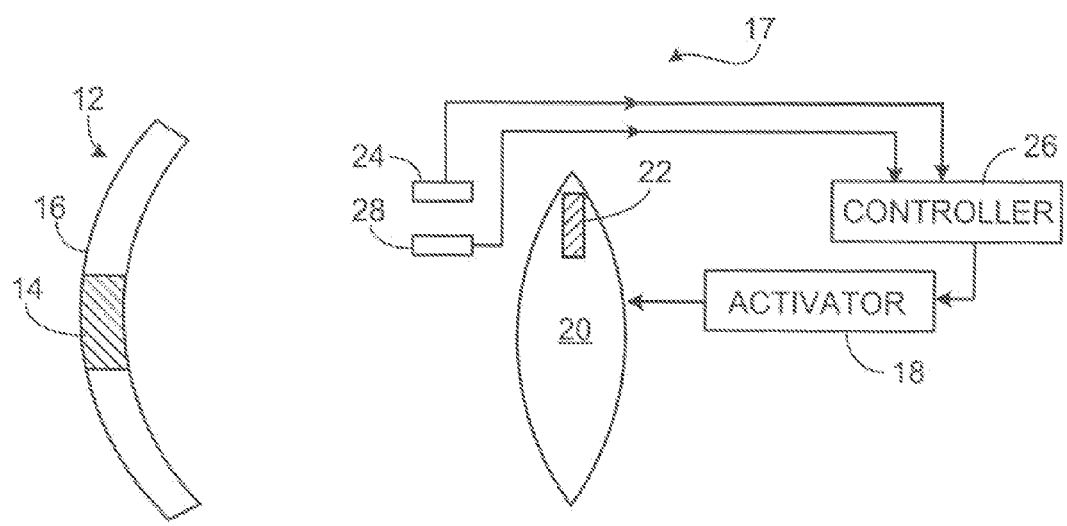
FIG. 3 shows an embodiment of a vision prosthesis with two detectors and one polarizing region.

In the block diagram of FIG. 3, a vision prosthesis 17 includes an actuator 18 for changing an optical property of an optical system 20. The optical system 20 can include the natural crystalline lens of the eye, an intraocular lens implanted in the eye, a contact lens, or an eyeglass lens. Exemplary lenses include the nematic crystal lenses described in U.S. Pat. No. 6,638,304, and the deformable and/or translatable lenses described in U.S. application Ser. No. 10/895,504, filed on Jul. 21, 2004. The contents of both are incorporate herein by reference.

A variety of actuators can be used in the vision prosthesis 16. These include the electrodes described in U.S. Pat. No. 6,638,304 and the artificial muscle actuators described in U.S. application Ser. No. 10/895,504, filed on Jul. 21, 2004.

In the vision prosthesis 17 shown in FIG. 3, the lens 20 has a polarizing region 22 that allows passage only of light having a first polarization state. A first detector 24 is disposed to sample light exiting the polarizing region 22. This first detector 24 provides, to a controller 26, a first signal indicative of the polarization state of that incoming light. A second detector 28 is disposed to sample light reflected from the retina 12. This second detector 28, provides to the controller 26, a second signal indicative of the polarization state of the reflected light. The first and second signals together provide an indication of the extent to which reflection from the retina 12 changes the polarization state of the polarized light incident thereon.

The controller 26 is calibrated such that the extent to which the fovea 14 by itself alters the polarization state of light incident thereon is known. On the basis of the first and second signals, and the calibration data, the controller 26 determines the relative contributions of the foveal and circumfoveal reflections to the light reflected from the retina 12. The controller 26 then generates a signal for causing the actuator 18 to change the focal length of the lens 20 so as to cause the foveal contribution to increase at the expense of the circumfoveal contribution.

Figure 4:
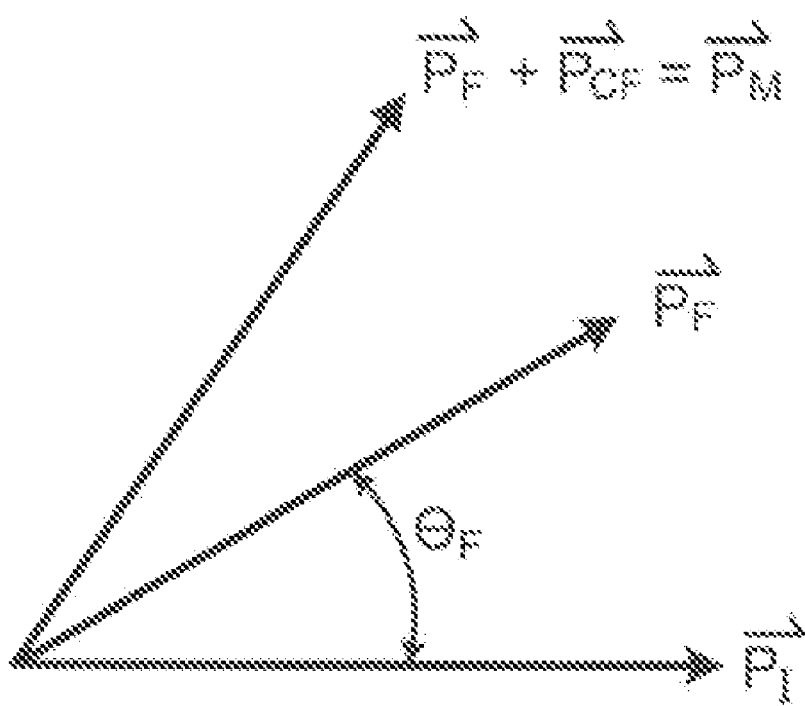
FIG. 4 illustrates resolution of polarization vectors.

FIG. 4 illustrates one way in which the controller 26 can determine the relative contributions of the foveal and circumfoveal reflections. A first polarization vector $P_I$ in FIG. 4 represents the polarization state of light incident on the retina 12, and a second polarization vector $P_F$ represents the polarization state of the foveal reflection. A third polarization vector $P_M$ corresponds to the measurement provided by the detector. This third polarization vector $P_M$ represents the combined effect of both the foveal and circumfoveal contributions to the reflection. It will be apparent that the foveal contribution is the projection of the third vector $P_M$ on the second vector $P_F$ and that the circumfoveal contribution is the remainder thereof.

In many cases, it will not be possible to determine in which direction the focal point should be moved. This is because it is not possible to determine, on the basis of the relative contributions of the foveal and circumfoveal contributions, whether the focal plane is anterior or posterior to the retina 12.

A person who attempts to focus a pair of binoculars encounters a similar problem. On seeing a blurry image, it is not apparent which way one must turn the focusing knob to bring the image into focus. Most people overcome this difficulty by turning the focusing knob in one direction and seeing if the image becomes more blurry, and then turning it in the opposite direction if it does so. Similarly, the controller 26 sends a signal to the actuator 18 to move the focal plane in one direction and observes the change in the relative contributions of the foveal and circumfoveal reflections. If the circumfoveal contribution increases at the expense of the foveal contribution, the controller 26 corrects itself by sending a signal to move the focal plane in the opposite direction.

Figure 5:
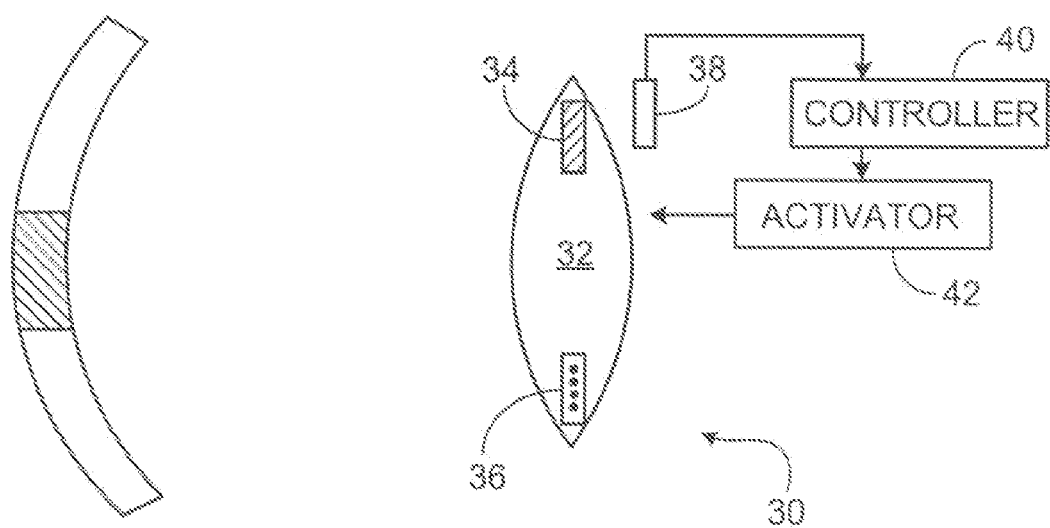
FIG. 5 shows an embodiment of a vision prosthesis with two polarizing regions and one detector.

Another embodiment of a vision prosthesis 30, shown in FIG. 5, features a lens 32 having first and second polarizing regions 36, 34 that impose orthogonal polarization states on incident light. For example, in one embodiment, the first polarizing region 36 passes only light polarized in a first direction and the second polarizing region 34 passes only light polarized in a second direction orthogonal to the first direction. Consequently, light exiting the second polarizing region 34 represents the polarizing effect of the retinal reflection, but with the polarizing effect of the first polarizing region 36 already removed. This light is then provided to a detector 38. On the basis of the detected light, the controller provides a signal to a controller 40. The controller 40 uses this signal to generate a control signal to cause an actuator 42 to adjust the focal length of the lens.

Figure 6:
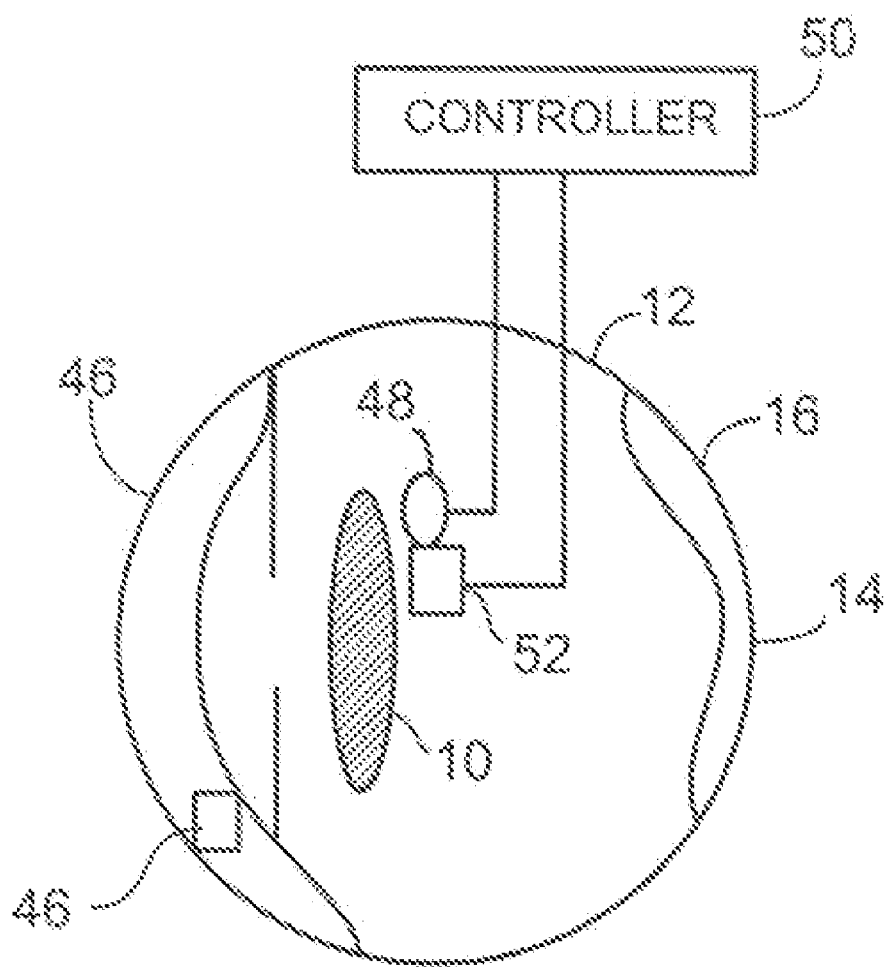
FIG. 6 is an embodiment in which polarization is provided by the cornea.

It is known that, to some extent, the cornea itself polarizes light. Another embodiment, shown in FIG. 6, takes advantage of this corneal polarization. In this embodiment, a first detector 44 is disposed to receive light passing through a cornea 46 and a second detector 48 is disposed to receive light reflected from the retina 12. Outputs of the detectors 44, 48 are then processed by a controller 50, which provides a control signal to an actuator 52 in the manner discussed in connection with FIG. 1.

Certain embodiments discussed above feature first and second detectors. In those embodiments, the functions of those detectors can be integrated into a single device.

In certain of the foregoing embodiments, one or more polarizing regions are integral with the lens. However, this need not be the case. The polarizing regions may be provided by discrete elements positioned in the optical path of the lens or a portion thereof. For example, the polarizing regions may be integrated into a flat plate that otherwise has no optical effect.

The foregoing description uses the term "lens" to refer to assemblies that may include one or more optical elements that cooperate to focus incident light. The term "lens" is not to be construed as necessarily being limited to a single refractive element.

At least some of the embodiments described herein can be used in conjunction with an intraocular lens, a contact lens, or an eyeglass lens.

Although the foregoing embodiments are shown with a single detector for sampling a light wave, it will be appreciated that several detectors can be provided for sampling a light wave at several locations on the lens.

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

Having described the invention, and a preferred embodiment thereof, what I claim as new, and secured by Letters Patent is:

1. A vision prosthesis comprising:
    a first polarization-sensitive detector disposed and configured to detect a polarization state of light reflected from a retina; and
    a controller in communication with the first detector, the controller being configured to receive, from the detector, a measurement signal indicative of the polarization state, and, in response thereto, to generate a controller signal for causing a change to an optical property of an optical system in optical communication with the retina.

2. The vision prosthesis of claim 1, further comprising a first polarizer for receiving light from the retina; the first polarizer blocking passage of light having a first polarization state.

3. The vision prosthesis or claim 2, wherein the first polarizer comprises a first polarizing region of a lens in the optical system.

4. The vision prosthesis of claim 2, further comprising a second detector disposed to detect light passing through the first polarizer, the second detector being configured to provide, to the controller, a signal representative of light passing through the first polarizer.

5. The vision prosthesis of claim 2, further comprising a second polarizer for receiving light from the retina, the second polarizer blocking passage of light having a second polarization state orthogonal to the first polarization state.

6. The vision prosthesis of claim 1, wherein the first detector is configured to be implanted in a cornea.

7. The vision prosthesis of claim 1, wherein the controller is configured to cause a change to an optical system that includes an intra-ocular lens.

8. The vision prosthesis of claim 1, wherein the controller is configured to cause a change to an optical system that includes a contact lens.

9. The vision prosthesis of claim 1, wherein the controller is configured to cause a change to an optical system that includes an eyeglass lens.

10. The vision prosthesis of claim 1, wherein the control is configured to change an optical property of a natural lens of the eye.

11. The vision prosthesis of claim 1, wherein the controller is configured to generate a control signal at least in part on the basis of a comparison between polarized light reflected from a foveal region of the retina and polarized light reflected from elsewhere on the retina.

12. The vision prosthesis of claim 1, wherein the controller is configured to generate a control signal on the basis of a comparison between the polarization state as detected by the first detector and a polarization state associated with light reflected from a fovea of the retina.

13. The vision prosthesis of claim 1, wherein the controller is configured to generate a control signal to cause a change to a focal length of the optical system.

\* \* \* \* \*